US008524262B2

United States Patent
Roy et al.

(10) Patent No.: US 8,524,262 B2
(45) Date of Patent: Sep. 3, 2013

(54) AMPHIPHILIC HIGH REFRACTIVE INDEX ORGANOPOLYSILOXANES

(75) Inventors: Aroop Kumar Roy, Saline, MI (US); Michael Lee Coffey, Adrian, MI (US)

(73) Assignee: Wacker Chemical Corporation, Adrian, MI (US)

( * ) Notice: Subject to any disclaimer, the term of this patent is extended or adjusted under 35 U.S.C. 154(b) by 206 days.

(21) Appl. No.: 13/032,883

(22) Filed: Feb. 23, 2011

(65) Prior Publication Data
US 2012/0213721 A1    Aug. 23, 2012

(51) Int. Cl.
*A61K 47/02*    (2006.01)
*A61K 47/34*    (2006.01)
*A61K 8/18*    (2006.01)
*A61K 8/25*    (2006.01)
*A61Q 5/00*    (2006.01)
*A61Q 5/12*    (2006.01)
*A61Q 19/00*    (2006.01)
*C07F 7/04*    (2006.01)
*C07F 7/08*    (2006.01)

(52) U.S. Cl.
USPC .......... 424/401; 424/64; 424/70.12; 514/772; 556/465

(58) Field of Classification Search
USPC ................ 424/70.12; 514/772; 556/645
See application file for complete search history.

(56) References Cited

U.S. PATENT DOCUMENTS 5,384,383 A    1/1995    Legrow et al.
6,133,370 A    10/2000   Gutek et al.

FOREIGN PATENT DOCUMENTS

EP    1 094 088 A1    4/2001

*Primary Examiner* — Ernst Arnold
(74) *Attorney, Agent, or Firm* — Brooks Kushman P.C.

(57) ABSTRACT

Amphiphilic silicons which are dispersible or self-dispersing in water, have a high refractive index, and are prepared by a hydrosilylation reaction, resulting in products which are free of cyclic organopolysiloxanes. The high refractive index and dispersibility make the amphiphilic silicones useful in personal care and cosmetics where high shine or gloss is desired.

28 Claims, No Drawings

AMPHIPHILIC HIGH REFRACTIVE INDEX ORGANOPOLYSILOXANES

BACKGROUND OF THE INVENTION

1. Field of the Invention

The present invention pertains to amphiphilic organopolysiloxanes having a high refractive index, which readily emulsify or self-emulsify in aqueous preparations to form micro- or macro-emulsions, are free of cyclic organopolysiloxanes, and bear arylalkyl, long chain alkyl, and hydrophilic groups along the polymer chain.

2. Background Art

Polydimethylsilicones, optionally functionalized, have long been used in a variety of applications including cosmetics and personal care products such as shampoos and conditioners. Unfortunately, such silicones suffer from a relatively low refractive index. In the personal care sector especially, there is an increasing emphasis on high gloss in hair care products. Such products also have uses in cleaning products such as waxes and polishes.

Personal care consumer products such as shampoos, conditioners, skin care formulations and color cosmetics articles often derive high or higher aesthetic and commercial value from the shine and/or gloss benefits that they impart. Ingredients with a refractive index (RI) of greater than about 1.44 can lead to distinct/discernible shine/gloss perception on keratinous and skin surfaces. Aryl substituents in both small molecules and polymers are a preferred way to raise the RI of ingredients used for shine in personal care formulations. High-RI arylated silicones (both homo- and copolymers with dimethylsiloxane) containing either Ar—Si moieties or aralkyl substitution on silicon are widely known in the literature and the personal care industry, although molecules with the Ar—Si unit are most commonly used in personal care, particularly, ingredients such as phenyl trimethicone (INCI nomenclature) and sold in the market, e.g., as Dow Corning® 556 Fluid.

Arylalkylsilicones of high refractive index are known from U.S. Pat. No. 5,384,383, and are prepared by hydrolytic condensation of 2-phenylpropylmethyldichlorosilanes. However, the preparation leads to high quantities of cyclic products which may be environmentally or toxicologically suspect. A comparative preparation by hydrosilylation of α-methylstyrene is taught by U.S. Pat. No. 5,384,383 to be deficient in that the product has a strong odor of α-methylstyrene.

It is of note that the above arylated and arylalkylated silicones are primarily used in the oil phase of the formulation due to their compatibility with common formulation ingredients such as natural oils, synthetic esters and hydrocarbons. The trend toward water-based formulations and especially clear, water-based formulations in personal care is steadily increasing, following the desire of the consumer to use more "natural" and "organic" products. There is, therefore, a distinct need to provide the benefit of shine/gloss via aryl-containing siloxanes that are compatible with or readily compatibilized in polar formulation media, particularly water, without significantly compromising oil compatibility. Such amphiphilic and versatile, arylalkyl-containing silicones of general utility have not been available commercially.

U.S. Pat. No. 6,133,370 discloses the preparation of silicones which contain both arylalkyl moieties and polyether moieties. However, the preparation methods enabled by the '370 patent all involve either a cohydrolytic condensation of appropriately substituted chlorosilanes or the use of an equilibration reaction, and thus the products all contain a significant proportion of suspect cyclic compounds. Only the introduction of the polyether moieties is achieved by hydrosilylation. In the process of the '370 patent, it is exceptionally difficult to remove arylalkylated cyclic species from the reaction product. There is no indication that the products of the '370 patent are capable of either self-emulsification in water or microemulsion formation, nor would they be expected to be.

SUMMARY OF THE INVENTION

Applicants have surprisingly and unexpectedly discovered that organopolysiloxanes with high refractive index which are free of cyclic organopolysiloxanes can be prepared in a one pot synthesis by hydrosilylation of an arylalkene, an ethylenically unsaturated polyether, and a long chain alkene, by reaction with a Si—H functional organopolysiloxane, with no equilibration or hydrolytic condensation being necessary. The resulting ter(or higher)polymers are dispersible in aqueous formulations to provide macro- or micro-emulsions, and are preferably self-emulsifying. They also, surprisingly, have no strong odor of arylalkenes.

DETAILED DESCRIPTION OF THE PREFERRED EMBODIMENTS

The organopolysiloxanes of the present invention contain arylalkylsiloxy moieties, siloxy moieties bearing at least one long chain alkyl group, siloxy moieties bearing a hydrophilic group, optionally lower dialkylsiloxy moieties, and are prepared by hydrosilylation, not by cohydrolysis or equilibration. Thus, they contain no objectionable quantity of cyclic organopolysiloxanes.

The organopolysiloxanes of the present invention generally correspond to the structural formula (I):

$$R_3SiO\,(R^1{}_2SiO)_w\,(R^1JSiO)_x\,(R^1KSiO)_y\,(R^1LSiO)_z\,SiR_3 \qquad (I)$$

wherein each R, independently of each other, is a $C_{1-30}$ hydrocarbon group, preferably an alkyl, cycloalkyl, aryl, arylalkyl, or alkaryl group having 1 to 30 carbon atoms, and in the case of R containing aryl groups, containing at least 5 ring atoms, in addition to which the aryl rings of the aryl, alkaryl, or arylalkyl group may also contain heteroatoms selected from the group of oxygen, sulfur, nitrogen, and phosphorus, or R may be another organic group or inorganic group which is substantially unreactive in hydrosilylation reactions or will not inhibit hydrosilylation, for example a hydroxyl group, acyloxy group, or alkoxy group, the alcohol moiety of the alkoxy group containing preferably from 1 to 4 carbon atoms, most preferably a methoxy or ethoxy group, or R is an L group. R is preferably a $C_{1-6}$ alkyl group, phenyl, phenylethyl, 2-phenylpropyl, or naphthylethyl group, and most preferably for reasons of economy, a methyl group.

$R^1$ each independently may be a $C_{1-30}$ hydrocarbon group, preferably an alkyl group, a cycloalkyl group, aryl group, arylalkyl group, or alkaryl group, wherein the aryl groups may contain heteroatoms as for R, more preferably a $C_{1-4}$ alkyl group, a phenyl group, or oxyalkyl group and most preferably a methyl group. $R^1$ may also be hydrogen, as a result of excess Si—H bound hydrogen in the H-siloxane reactant, or as a result of incomplete reaction.

The group J is an arylalkyl moiety which is the residue of a compound able to be attached to the organopolysiloxane backbone by a hydrosilylation reaction. J is preferably phenylethyl, 2-phenylpropyl, 3-phenylbutyl, or naphthylethyl. Most preferably, J is 2-phenylpropyl. It is preferred that the $R^1$ moiety in the $R^1JSiO$ siloxy units is methyl or phenyl, and the R¹JSiO siloxy units are preferably substituted such that the starting organohydrogen-polysiloxane does not need to contain any substantial quantities of H₂SiO groups, or siloxy groups bearing both Si—H bound hydrogen and an organic group other than methyl or phenyl, which would increase expense. In the preferred polymers, in the R¹JSiO siloxy groups, R¹ is phenyl or $C_{1-4}$ alkyl, preferably methyl. Groups J preferably have 8-30 carbon atoms, more preferably 9-13 carbon atoms.

K is a long chain alkyl group having at least 6 carbon atoms, preferably at least 8 carbon atoms, and preferably not more than 45 carbon atoms, more preferably not more than 30 carbon atoms. K is preferably a $C_8$ to $C_{20}$ alkyl group, more preferably a $C_8$ to $C_{18}$ alkyl group. The K groups are derived from hydrosilylation of the appropriate alkene, such as 1-octene, 1-dodecene, 1-octadecene, etc. As with the R¹JSiO siloxy units, in the R¹KSiO siloxy units, it is preferred that R¹ is methyl or phenyl.

The group L is a hydrophilic species, which, in conjunction with the hydrophobic species J, K, and when present, R or R¹ species which are aryl, cycloalkyl, arylalkyl, or alkaryl, confer amphiphilic properties, in particular ready emulsifying properties and/or self-emulsifying properties. In the amphiphilic silicones L may be independently selected from Si—C-bonded polyoxyalkylene polyethers having the formula (II)

$$—R^a—O—(R^bO)_c—X \qquad (II)$$

wherein $R^a$ is an alkylene or alkenylene radical which is Si—C bonded, $R^b$ is a divalent hydrocarbon radical, and X is a terminal group which does not interfere with hydrosilylation, and c is such that the polyoxyalkylene polyether has a molecular weight of from 300-6000; a polyhydroxy compound of the formula

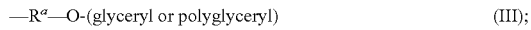

$$—R^a—O\text{-(glyceryl or polyglyceryl)} \qquad (III);$$

a saccharidyl group of the formula —$R^a$—O-(monosaccharide or polysaccharide) (IV); and a polyvinylalcohol homopolymer or copolymer of the formula —$R^a$-(polyvinylalcohol homo or copolymer) (V).

The groups L are, independently of one another, hydrophilic species which contain a plurality of hydroxyl groups or are polyether groups, or mixtures thereof. L are bonded through an alkylene or alkylenyl group derived from hydrosilylation of an alkenyl or alkynyl group bonded to the hydrophilic moiety of the L group, and are preferably selected from polyoxyalkylene polyethers terminated on one end with a hydrosilylatable group, preferably a vinyl or allyl group, and terminated on the other end by alkyl, aryl, alkaryl, aralkyl, hydroxyl, alkoxy, carboxy, or other groups such as sulfate ester, phosphate ester, or other terminating groups which do not interfere with a hydrosilylation reaction. L may also contain a glyceryl or polyglyceryl species, a monosaccaridyl or polysaccharidyl species or polyvinylalcohol species, for example. The groups L are groups derived from hydrosilylation of an unsaturated compound containing the hydrophilic moiety.

For example, and by preference, the L group may be an alkylpolyether moiety —$R^2$—O(CH₂CH₂)$_p$—($C_3H_6O$)$_q$ ($C_nH_{n+2}O$)$_r$—$R^b$ wherein $R^2$ is a $C_2$-$C_{20}$ divalent hydrocarbon group, n is 4-10, and $R^b$ is preferably a $C_{1-20}$ hydrocarbon, more preferably an alkyl, cycloalkyl, aryl, arylalkyl, or alkaryl group or a hydroxyl or acyl group, and most preferably a hydroxyl, methyl, butyl, or acetyl group. To be hydrophilic, the p and q groups must dominate, preferably the p groups. The variables p and q have values in the range of 0-30, preferably 0-20 but at least one p, q, or r group must be present. Most preferably, r is less than 4 and preferably 0, q is less than or equal to about 20 (on average). The sum of p+q+r must be about 6 or higher, and the molecular weight of L preferably ranges from about 300 to about 6000. The p, q, and r units may be present randomly distributed, as homopolymeric blocks, as heteric blocks, or in any desired distribution. If homopolymeric oxypropylene or oxy(higher alkylene) blocks are employed, such blocks cannot be so long as to confer hydrophobicity rather than hydrophilicity or a combination of hydrophilicity and oleophilicity. For example, it is relatively well known that polyoxypropylene homopolymer polyethers with molecular weights above 400-500 Daltons are oily and hydrophobic, whereas low molecular weight analogues such as propylene glycol, dipropylene glycol, and tripropylene glycol are quite hydrophilic. In the case of higher polyoxyalkylenes such as polybutylene glycol, e.g., polytetramethylene glycol, the higher carbon to oxygen ratio renders such oligoethers and polyethers hydrophobic at yet lower molecular weights. Thus, homopolyoxyethylene glycol and copoly(oxyethylene/oxypropylene) glycols, copoly(oxyethylene/oxybutylene) glycols, or terpoly(oxyethylene/oxy-propylene/oxybutylene) glycols are preferred. Again, it is the ready dispersibility of the product which is of paramount importance. This dispersibility is easily assessed, as indicated subsequently. The use of block copolyethers or block/heteric copolyethers derived from ethylene oxide and propylene oxide may be particularly useful, as these groups are known not only to be hydrophilic, but also to provide emulsification (i.e. surface-active) properties.

L may also contain a glyceryl or other highly hydroxyl group-containing species such as a derivative of pentaerythritol, polyglycerine, a saccharide or polysaccharide, or the like. Glycosyl species are particularly preferred. Species such as glycerine, polyglycols, polyglycerols, oligo and polysaccharides, and polyvinyl alcohol, all hydrophilic species, may be derivatized by conventional techniques in organic chemistry to generate a derivative having at least one and preferably substantially only one ethylenically (or ethylynically) unsaturated, hydrosilylatable group. Thus, for example, vinyl groups, allyl groups, acrylato or methacrylato groups may be present in these derivatives. In the case of the polyethers, the polyethers may be synthesized by oxyalkylation of allyl alcohol or another unsaturated alcohol. In the case of hydroxyl-functional hydrophilic groups such as glyceryl, polyglyceryl, saccharidyl, or polyvinyl alcohol, the base substances can be etherified or esterified with unsaturated groups, or reacted with unsaturated isocyanates or the like, to introduce the necessary ethylenic or ethylynic unsaturation.

The polyvinylalcohol hydrophilic moieties may be homopolymeric or copolymeric. Polyvinylalcohols are generally prepared by hydrolysis of polyvinyl esters, predominately polyvinyl acetate, polyvinylpropionate, and mixed polyvinyl(acetate/propionate). The hydrolysis may be substantially complete, i.e. from 95-99 mol percent or more complete, or may be partial. The greater the content of remaining ester groups, the less hydrophilic is the resulting polymer. The polyvinyl alcohols, whether completely hydrolyzed or not, may also be modified, for example by acetalization with aldehydes such as formaldehyde, acetaldehyde, propionaldehyde, or butyraldehyde. The higher the degree of acetalization, the less hydrophilic the copolymer. In addition, copolymer polyvinyl alcohols may be prepared by hydrolyzing a mixed polyvinyl ester polymer such as a copolymer of ethylene and vinyl acetate. The more ethylene units are present, the less hydrophilic is the copolymer following hydrolysis. Other monomers which result in groups which do not interfere with a hydrosilylation reaction may also be present. Whether a particular group interferes with hydrosilylation can be routinely determined by hydrosilylating the copolymer, bearing an unsaturated carbon-carbon bond as described previously, in a test hydrosilylation of this one component with an Si—H functional organopolysiloxane. By choice of appropriate comonomers, derivatization (such as by acetalization), and by adjusting the degree of hydrolysis of vinyl ester groups, a wide range of hydrophilicity can be obtained.

The amphiphilic silicones of the invention may also contain chain extending groups and crosslinking or branching groups containing a silicon-carbon bonded hydrocarbon radical or hydrophilic group. The chain extending groups may be prepared, for example, by reaction of an H-siloxane containing SiH-functional terminal groups with a compound bearing two hydrosilylatable unsaturated groups. Examples of such compounds are divinylbenzene, α,ω-dienes, and α,ω-allyl-terminated polyoxyalkylene polyethers. Essentially, these bis-unsaturated groups correspond to the R, $R^1$, J, K, and L groups discussed previously, but containing at least two sites of carbon-carbon unsaturation.

Thus, the preferred chain extending groups correspond to those of the formula $$[O_{1/2}R^1_2Si\text{—}R'\text{—}SiR^1_2O_{1/2}]_t \quad (VI)$$

where t is 0-100, preferably 0-50, more preferably 0-20, yet more preferably 0-5, and most preferably 0-3. Preferably, no chain extending groups are present, except as unavoidable linkages formed from impurities in the reactive components. R' is a hydrocarbon radical having 4-30 carbon atoms SiC bonded to both silicon atoms of the chain extending group, or a hydrophilic group SiC bonded to both silicon atoms through a $C_{2-20}$ hydrocarbon linkage, preferably a $C_{2-4}$ hydrocarbon linkage. The R' units may also be defined as J', K', and L' groups, as may also be the R' groups of branching structures described above, these J', K', and L' groups corresponding to the definitions of the J, K, and L groups, but carrying an additional site of hydrosilylatable unsaturation.

The branching or crosslinking groups preferably are those of the formula

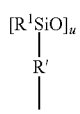

(VII)

where u is 0-100, preferably 0-50, more preferably 0-20, yet more preferably 0-5, and most preferably 0-3. In the branching groups, R' is a divalent branching moiety which links the branching unit via R' with at least one other siloxy group so as to form a branch in the organopolysiloxane at this point. The at least one other siloxy group may be the terminus of an organopolysiloxane chain, or may be a siloxy group within an organopolysiloxane chain. Thus, dendrimer and ladder like branched and crosslinked polymers may be formed.

The chain extension may be used to control the molecular weight, but it is difficult to do so without also increasing the amount of branching and crosslinking. The larger the amount of chain extension, the higher the molecular weight and viscosity. Increasing branching also in general leads to higher viscosities, while crosslinking can render the silicones swellable but insoluble in oil phases. Thus, both chain extension and branching/crosslinking can be used to tailor polymer properties.

The bis-hydrosilylatable compounds which ultimately form the R' groups of the chain extending and branching/crosslinking groups can be added at any time during preparation of the amphiphilic silicones of the invention. Unless added in very small amounts, however, it is desirable that they be added toward the end of the synthesis, since branching and crosslinking may interfere with the ease of hydrosilylation or may cause solubility problems. The R' group precursors may be added both at the beginning and toward the end of the reaction. When branching groups or chain extending groups are present, it is preferred that the R' groups be derived from bis(alkenyl or alkynyl) hydrophilic moieties. One such preferred moiety is an α,ω-bis(allyl) terminated polyoxyalkylene polyether, as described earlier for the L groups of the amphiphilic silicone.

The preparation of such hydrosilylatable derivatives containing hydrophilic groups and hydrosilyatable carbon-carbon multiple unsaturation is known from conventional organic chemistry and well known to those skilled in the art. Preferably, L is an oxygen-containing, Si—C bonded hydrophilic group having a molecular weight of 100 Daltons or more. In a preferred embodiment, the inventive amphiphilic silicones are those which are preparable by reacting hydrosilylatable compounds which will supply the groups J, K, and L, with a polysiloxane whose internal repeating units are substantially dimethylsiloxy, methylhydrogensiloxy, and optionally but not preferably, dihydrogensiloxy units. The H-siloxane may or may not contain Si—H bound hydrogen in its terminal units as well. Polysiloxanes containing methylphenylsiloxy, diphenylsiloxy, and phenylhydrogen siloxy groups in addition or in lieu of to the groups just mentioned are also preferred. The terminal groups are preferably trimethylsilyl groups, but any suitable terminal group which does not interfere with hydrosilation may be used, for example dimethylphenylsiloxy, hydrogendimethylsiloxy, hydroxyldimethylsiloxy, etc. Such Si—H-containing siloxanes, sometimes termed "H-siloxanes" are readily available commercially, or can be synthesized by methods well known in organosilicon chemistry. For reasons or economy, the H-siloxanes are preferably poly(methylhydrogensiloxy/dimethylsiloxy) silicones with trimethylsilyl termination, for example those of the formula $$A\text{-}[OSiMe_2]_d[OSiHMe]_e\text{O-}A$$

where A independently is $HMe_2Si$ or $Me_3Si$, and where e is preferably equal to the sum of x, y, and z, and the sum of d and e is such that the desired molecular weight and/or chain length is obtained. In other words, preferably substantially all of the groups J, K. and L are bonded to the amphiphilic silicone by hydrosilylation with the H-siloxane. However, it is also possible that the H-siloxane may contain some of the groups J, K. and L already as R' groups, i.e. prior to hydrosilylation. For reasons of economy, this is not preferable.

The amphiphilic silicones of the subject invention are prepared through hydrosilylation of J, K. and L precursors, these precursors containing a hydrosilylatable carbon-carbon multiple bond. The hydrosilylation may be concerted, pseudoconcerted, or completely stepwise relative to the addition of reactants, but is preferably stepwise. The order of hydrosilylation is not critical, but it is preferred that the arylalkene be reacted first, followed by the alkene, and finally by the alkenyl-functional hydrophilic species. It has been found that when the alkene is reacted last, that significant isomerization may occur, requiring a higher amount of alkene.

The hydrosilylation catalyst may be any useful hydrosilylation catalyst. Most hydrosilylation catalysts are noble metals, or compounds or complexes of noble metals, e.g., rhodium, iridium, palladium or platinum, but platinum compounds are generally preferred due to their generally higher activity.

For example, as hydrosilylation catalysts it is possible to use metals and their compounds, such as platinum, rhodium, palladium, ruthenium, and iridium, preferably platinum and rhodium. The metals may optionally be fixed to finely divided support materials, such as activated carbon, metal oxides, such as aluminum oxide or silicon dioxide. Preference is given to using platinum and platinum compounds. Particular preference is given to those platinum compounds which are soluble in polyorganosiloxanes. Soluble platinum compounds that can be used include, for example, the platinum-olefin complexes of the formulae $(PtCl_2.olefin)_2$ and $H(PtCl_3.olefin)$, preference being given in this context to the use of alkenes having 2 to 8 carbon atoms, such as ethylene, propylene, isomers of butene and of octene, or cycloalkenes having 5 to 7 carbon atoms, such as cyclopentene, cyclohexene, and cycloheptene. Other soluble platinum catalysts are the reaction products of hexachloroplatinic acid with alcohols, ethers, and aldehydes or mixtures thereof, or the reaction product of hexachloroplatinic acid with methylvinylcyclotetrasiloxane in the presence of sodium bicarbonate in ethanolic solution. Platinum catalysts with phosphorus, sulfur, and amine ligands can be used as well, e.g., $(Ph_3P)_2PtCl_2$. Particularly preferred are complexes of platinum with vinylsiloxanes, such as sym-divinyltetramethyldisiloxane. Other hydrosilylation catalysts are known from the patent and non-patent literature.

The hydrosilylation catalyst may be all initially present at the onset of the reaction, may be partially present initially with additional catalyst metered in or may be added incrementally, preferably added incrementally corresponding to the addition steps of the various reactants. The amounts of catalyst are conventional, for example 1 to 5000 ppm relative to the final product weight and based on elemental noble metal, more preferably 10 to 500 ppm, and most preferably about 50-250 ppm. The amounts are easily adjusted by one skilled in the art, for example by observing the rate of reaction or by measuring unreacted starting materials. Selection of an appropriate amount of catalyst is well within the skill of the art.

The hydrosilylation reaction may take place neat, or in organic solvent. Neat preparation is preferred. The temperature is conventional, and may range, for example, from 20° C. to 200° C., preferably 50° C. to 180° C. Following the reaction, the product may be stripped of residual solvents and other volatiles by stripping under vacuum or with an inert gas such as nitrogen, or by use of conventional processing, for example by employing a falling film evaporator or wiped film evaporator.

The convenient, one-pot chemistry to prepare the products of this invention preferably involves sequential hydrosilation reactions with a poly(methylsiloxane) or a poly(methylsiloxane-co-dimethylsiloxane) using an aralkene, alkene, and typically a monoallyl ether of a polyalkyleneoxide and/or other polyhydroxy compound as the unsaturated substrates. Preferred hydrosilation catalysts are platinum compounds or complexes, such as Speier's catalyst or Karstedt's catalyst or modified versions of these.

The ratio w:x:y:z in formula I can be important with respect to producing a liquid or solid product vs. a gel-like and unprocessable material, depending on the hydrosiloxane used for the hydrosilation. For those skilled in the art, a more desirable liquid product or a soft solid can be ensured via routine experimentation. In the amphiphilic silicones, w is 0 to 200, preferably 0 to 100, and more preferably 0 to 50; x is from 1-100, preferably 1 to 50, and more preferably 1 to 25; y is 1 to 50, preferably 1 to 25, and more preferably 1 to 10; and z is 1-50, preferably 1 to 25, and more preferably 1 to 10.

Silicone-in-water (Si/W) emulsions can be readily prepared with the compositions of this invention. Particularly, Si/W micro-emulsions of the internal silicone phase particle size of 30-55 nm were achievable using common and commercially available surfactants and mixtures of surfactants. Silicone content of these emulsions can be 15-20% w/w or higher.

Even more surprisingly, compositions of this invention were self-emulsifying in water at 15% w/w or higher, depending on the ratio w:x:y:z and the nature of the long-chain hydrocarbyl and polar polyoxyalkylene or polyhydroxy substituents, which can be determined through routine experimentation by one skilled in the art.

Of equal surprise was the ability to add the amphiphilic silicones of this invention directly at 2-5% w/w levels to multiple commercial, water-clear shampoos from several manufacturers without producing any haze to the commercial formulations. Although thinning of these shampoos was observed, this can be addressed via multiple means by those skilled in the art. The same compatibility with the commercial shampoos was observed with micro-emulsions produced from the amphiphilic silicones.

Bleached European hair swatches sprayed with a simple pump-spray formulation containing 2% amphiphilic silicone of this invention showed distinct gloss vs. an untreated hair swatch and one treated with the solvent alone.

Thus, the compositions of this invention offer a new class of shine/gloss-enhancing amphiphilic silicones that have not been previously available. As such, these are suitable for use in oil- or water-based hair care, skin care, and color cosmetics formulations, such as shampoos, conditioners, hair shine sprays, pomades, mousses, gels, creams, skin care lotions and creams, moisturizers, bath oils, body washes, soaps, aftershave products, lipsticks, lip colors, lip glosses, eyeshadows, mascaras, eyeliners, blushes, foundations and other facial make-ups, pressed-powders and various make-up removers, either as straight fluids or in emulsion form. They are also suitable for use in waxes, polishes, tire glosses and other uses.

An advantage of the amphiphilic silicones of the invention and their preparation process is that they are substantially free of low molecular weight cyclosiloxanes, and these in fact are generally undetectable. A further advantage is that the products do not have the strong odor of arylalkanes such as styrene or α-methylstyrene, despite the use of hydrosilylation to prepare the silicones. By "free of cyclics means that the content of volatile cyclics is less than 0.5 weight percent based on the total weight of the amphiphilic silicone. More preferably, the cyclics content is less than 0.1 weight percent and yet more preferably less than 0.05 weight percent. Most preferably no volatile cyclosiloxanes are detectable by $^1$H-NMR or $^{29}$Si-NMR.] By "low molecular weight" is meant cyclosiloxanes which have a significant vapor pressure at 25-37° C., in particular cyclosiloxanes with 5 silicon atoms or less, such as cyclotrisiloxanes, cyclotetrasiloxanes, and cyclopentasiloxanes Low molecular weight linear species such as oligosiloxanes containing four silicon atoms or less are also preferably absent or at very low concentrations.

The invention will now be illustrated by examples, which are not to be construed as limiting the invention in any way.
General apparatus set-up:

A 4-neck round-bottomed flask, equipped with various neck adapters and stopcock-equipped bypass adapter and Teflon® PTFE neck-sleeves to accommodate a mechanical stirrer, thermocouple, addition funnel, water condenser, nitrogen gas inlet and outlet, and rubber septum was used for the hydrosilation. A heating mantle was used for heating the flask. An electronic thermostat was used in conjunction with the thermocouple to control heating of the flask and contents. The preparation was conducted under a mild flow of dry nitrogen gas. Upon completion of reaction, the water condenser was by-passed or removed and any volatiles were removed under vacuum. The product was cooled to 40° C. and filtered under air or nitrogen pressure using a 0.45-1 μm nylon or Teflon membrane filter with or without a pre-filter.

EXAMPLE 1

The reaction flask was charged with a poly(methylsiloxane-co-dimethylsiloxane) [300 g, H content 0.642% w/w]. The flask was heated to 80° C., alpha-methylstyrene (AMS, 112.6 g) was charged to the addition funnel and approx. one-third of the AMS was added to the flask while raising the temperature of the flask contents to about 120-125 ° C. At 125° C., a solution of chloroplatinic acid in cyclohexanol (1% Pt w/w in the cyclohexanol solution, 120 μL) was added quickly to the stirring (200-250 rpm) mixture in the flask via a syringe. A rapid exotherm ensued and AMS addition from the funnel was continued to keep the temperature in the range 140-160° C. from the heat of reaction. Upon completion of AMS addition, a further aliquot of Pt catalyst (120 μL) was added and the mixture heated at 145° C. for 30 minutes. The temperature was then lowered to 125-130° C., and 1-octene (54.5 g) was added slowly from the addition funnel to maintain the temperature below about 140° C. The mixture was heated for 30 minutes at 140° C. The temperature was then set to 150° C. and poly(ethyleneoxide) monoallyl ether, 10 mol EO, (249.5 g) addition was begun. A further aliquot of catalyst (120 μL) was added following start of polyether addition, the temperature was raised to 155° C. halfway through the addition and the polyether addition was completed without allowing the temperature to drop below about 150° C. A fourth aliquot of catalyst (120 μL) was added, the mixture heated for one hour, a half aliquot of catalyst (60 μL) was added and the mixture heated for an additional hour, maintaining the temperature preferably in the range 150-155° C. throughout the 2 hour mixing. The reaction mixture was then stripped under vacuum (10-15 mm Hg) at about 155° C. to remove any residual volatile olefin. The off-white to straw-yellow product was then filtered after cooling to 40° C. to yield a nearly colorless and transparent liquid. $^1$H NMR analysis showed the expected product. GC-MS analysis showed residual AMS content to be below 100 ppm. Viscosity, 268 mPa·s. Refractive Index, 1.4615. Volatiles, 0.03% w/w.

EXAMPLE 2

Using a procedure very similar to that of Example 1, a poly(methylsiloxane-co-dimethylsiloxane) [58.5 g, 0.64% w/w H content] was allowed to react with AMS (21.8 g), 1-octadecene (24.4 g) and allyl-terminated polyethyleneoxide, 10 mol EO (48.8 g), in that order of addition. The addition temperature for octadecene addition was 145° C. and the Pt catalyst used was hexachloroplatinic acid in propylene glycol (0.5% w/w Pt, total catalyst volume 216 μL). The crude product was stripped under vacuum at 20 mm Hg and 160° C. and filtered to yield a clear, nearly colorless liquid. NMR analysis showed the expected product. Viscosity, 290 mPa·s. Refractive Index, 1.4603.

EXAMPLE 3

Using a procedure very similar to that of Example 1, a poly(methylsiloxane-co-dimethylsiloxane) [83 g, 0.64% w/w H content] was allowed to react with AMS (15.6 g), 1-octene (15.1 g) and monoallyl-terminated polyethyleneoxide, 10 mol EO (137.4 g), in that order of addition. The start temperature for octene addition was 130° C. and the Pt catalyst used was hexachloroplatinic acid in propylene glycol (0.5% w/w Pt, total catalyst solution volume 276 μL). The crude product was stripped under vacuum at 18 mm Hg and 160-166° C. and filtered to yield a clear, nearly colorless liquid. NMR analysis showed the expected product. Viscosity, 757 mPa·s. Refractive Index, 1.4572.

EXAMPLE 4

Using a procedure very similar to that of Example 1, a poly(methylsiloxane-co-dimethylsiloxane) [105 g, 0.656% w/w H content] was allowed to react with AMS (40.2 g), 1-octene (19.5 g) and monoallyl-terminated poly(ethyleneoxide-co-propyleneoxide), 20 mol EO-20 mol PO (316.6 g), in that order of addition. The start temperature for octene addition was 130° C. and the Pt catalyst used was chloroplatinic acid in cyclohexanol (1% w/w Pt, total catalyst volume 194 μL). The addition of the polyether was started at 155° C., half was added at this temperature and half was added at 160° C. Following completion of polyether addition, the mixture was stirred for two hours (at 160° C. in this example) as in Examples 1-3. The crude product was stripped under vacuum at 20 mm Hg and 160° C. and filtered (0.8 μm Nylon membrane filter) to yield a clear, colorless liquid. NMR analysis showed the expected product. Viscosity, 410 mPa·s. Refractive Index, 1.4580. Volatiles, 0.03% w/w.

EXAMPLE 5

Using a procedure very similar to that of Example 1, a poly(methylsiloxane) [34.6 g, 1.6 w/w H content] was allowed to react with AMS (11.6 g), 1-dodecene (58.3 g) and monoallyl-terminated polyethyleneoxide, 10 mol EO, (58.8 g), in that order of addition. The start temperature for dodecene addition was 145° C. and the Pt catalyst used was a modified version of Karstedt's catalyst diluted 50% v/v with AMS (0.5% w/w Pt, total catalyst volume 365 μL). The crude product was stripped under vacuum at 18 mm Hg and 160-168° C. and filtered to yield a slightly hazy, nearly colorless liquid. NMR analysis showed the expected product. Viscosity, 4100 mPa·s. Refractive Index, 1.4629.

EXAMPLE 6

Using the product of Example 2, a silicone-in-water (Si/W) micro-emulsion was prepared. Thus, into a beaker containing de-ionized water (7.32 g), were added with constant shearing, the surfactants Genapol X 100 (8.78 g), Lutensol TO5 (1.0 g), Lutensol AT25 (1.0 g) in that order, followed by the silicone fluid (15 g), glycerin (1.0 g) and water (65.9 g). The wall of the beaker was scraped as needed to ensure complete incorporation of the grease phase into the emulsion, and the temperature of the mixture was not allowed to rise above about 60° C. The emulsion was filtered after cooling as needed. This yielded a completely transparent micro-emulsion of the silicone fluid. Particle size of internal silicone phase, 33 nm (Malvern, Z average).

EXAMPLE 7

Using a procedure identical to Example 6, a silicone fluid of the structure and composition of Example 1 yielded a translucent micro-emulsion. Particle size of internal phase, 55 nm (Malvern, Z average).

EXAMPLE 8

In a manner similar to Example 6, the silicone fluid of Example 7 yielded a macro-emulsion using the composition: water—7.32 g, Genapol X 100—11.18 g, Lutensol TO5—1.3 g, Lutensol AT25—1.3 g, silicone fluid—15 g, glycerin—1.3 g, and water—62.6 g. Particle size of internal phase, 87 nm (Malvern, Z average).

EXAMPLE 9

The silicone fluid of Example 3 readily self-emulsified at 15% w/w in deionized water to a translucent emulsion.

EXAMPLE 10

The silicone fluid of Example 4 readily self-emulsified at 10% w/w in de-ionized water to a translucent emulsion.

Solubility of Wacker® TN (an alkyl-aralkyl silicone fluid) and compositions of present invention at 10% w/w at room temperature in various common personal care solvents. S—soluble, I=insoluble, SC=slightly cloudy.

| Solvent | Wacker® TN Fluid | Amphiphilic Silicone, Example 1 | Amphiphilic Silicone, Example 2 | Amphiphilic Silicone, Example 4 |
|---|---|---|---|---|
| Water | I | I | I | Self-emulsifying |
| Ethanol | I | S | S | S |
| Isopropanol | I | S | S | S |
| Dicaprylyl carbonate | I | S | S | S |
| C12-15 alkyl benzoate | S | S | S | S |
| Isopropyl palmitate | S | S | S | S |
| Castor oil | S | S | SC | SC |
| Light mineral oil | S | S | S | I |
| Decamethylcyclopentasiloxane | S | SC | S | I |
| Isododecane | S | S | SC | I |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. Amphiphilic silicone compositions, comprising at least one amphiphilic silicone (I) comprising groups of the formulae:

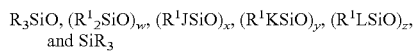

wherein
R is a group L or a $C_{1-30}$ hydrocarbon group, one R of the $R_3SiO$— or —$SiR^3$ group is optionally a hydroxyl group, and one or more R of the $R_3SiO$— or —$SiR^3$ group is/are optionally a $C_{1-8}$ alkoxy group;
$R^1$ is hydrogen or a $C_{1-30}$ hydrocarbon group;
J is an arylalkyl group;
K is a long chain $C_{8-45}$ alkyl group;
L is an Si—C bonded, oxygen-containing hydrophilic group having a molecular weight greater than 100 Daltons;
w is from 0 to 200;
x is from 1-100;
y is from 1 to 50; and
z is from 1 to 50,
with the proviso that the amphiphilic silicones contain less than 5 mol percent, based on the total mols of w,x,y, and z, of $RSiO_{3/2}$ groups and $SiO_{4/2}$ groups which form branching sites, and wherein the amounts of groups containing J and K are such that the amphiphilic silicone has a refractive index greater than 1.44, with the further proviso that the amphiphilic silicones are emulsifyable in water, and are substantially free of low molecular weight cyclosiloxanes.

2. The amphiphilic silicone of claim 1, wherein R is independently selected from the group consisting of methyl, ethyl, $C_{1-4}$ alkoxy, hydroxyl, and phenyl.

3. The amphiphilic silicone of claim 1, wherein $R^1$ are methyl or phenyl.

4. The amphiphilic silicone of claim 1, wherein J is selected from the group consisting of 2-phenylethyl, 2-phenylpropyl, 3-phenylbutyl, 2-naphthylethyl, and mixtures thereof.

5. The amphiphilic silicone of claim 1, wherein K is a $C_{8-26}$ alkyl group.

6. The amphiphilic silicone of claim 1, wherein L is independently selected from the group consisting of Si—C-bonded polyoxyalkylene polyethers having the formula (II)

$$-R^a-O-(R^bO)_c-X \qquad (II)$$

wherein
$R^a$ is an alkylene or alkenylene radical which is Si—C bonded,
$R^b$ is a divalent hydrocarbon radical, and X is a terminal group which does not interfere with hydrosilylation, and c is such that the polyoxyalkylene polyether has a molecular weight of from 300-6000;
a polyhydroxy compound of the formula $$-R^a-O\text{-(glyceryl or polyglyceryl)},$$

wherein $R^a$ is an alkylene or alkenylene radical which is Si—C bonded;
a saccharidyl group of the formula $$-R^a-O\text{-(monosaccharide or polysaccharide)};$$

wherein $R^a$ is an alkylene or alkenylene radical which is Si—C bonded, and a polyvinylalcohol homopolymer or copolymer of the formula $$-R^a\text{-(polyvinylalcohol homo or copolymer)},$$

wherein $R^a$ is an alkylene or alkenylene radical which is Si—C bonded.

7. The amphiphilic silicone of claim 6, wherein at least one group L is selected from the group consisting of hydrophilic alkylene-bonded polyoxyalkylene polyethers containing oxyethylene repeating groups and optionally oxypropylene repeating units.

8. The amphiphilic silicone of claim 7, wherein R and $R^1$ are methyl or phenyl, with the proviso that $R^1$ is also optionally silicon-bonded hydrogen in an amount of less than 10 mol percent based on the mols of w,x,y, and z repeating units.

9. The amphiphilic silicone of claim 1 which is self-dispersible in water.

10. The amphiphilic silicone composition of claim 1, which is in the form of an aqueous dispersion.

11. The amphiphilic silicone composition of claim 1, which is in the form of a silicone-in-water micro-emulsion.

12. The amphiphilic silicone of claim 1, wherein
w is from 3 to 200,
x is from 5 to 100,
y is 5-40, and
z is 3-20.

13. The amphiphilic silicone composition of claim 1, wherein the amphiphilic silicone further comprises at least one group of the formulae $$[O_{1/2}R^1{}_2Si—R'—SiR^1{}_2O_{1/2}]_t \quad (VI)$$

where t is up to 100
or

   (VII)

where R' is an Si—C bonded divalent hydrocarbon radical having from 4 to 30 carbon atoms, or hydrophilic group SiC bonded through a $C_{2-20}$ hydrocarbon linkage, and u is up to 100.

14. The amphiphilic silicone composition of claim 1, wherein the amphiphilic silicone has a refractive index of 1.4572 or greater.

15. The amphiphilic silicone composition of claim 1, wherein the amphiphilic silicone contains ($R^1{}_2SiO$) groups wherein $R^1$ is phenyl.

16. The amphiphilic silicone composition of claim 1, wherein the amphiphilic silicone contains at least one group L selected from the group consisting of a polyhydroxy compound of the formula —$R^a$—O-(glyceryl or polyglyceryl), wherein $R^a$ is an alkylene or alkenylene radical which is Si—C bonded;
a saccharidyl group of the formula —$R^a$—O-(monosaccharide or polysaccharide);

wherein $R^a$ is an alkylene or alkenylene radical which is Si—C bonded,
and a polyvinylalcohol homopolymer or copolymer of the formula —$R^a$-(polyvinylalcohol homo or copolymer), wherein $R^a$ is an alkylene or alkenylene radical which is Si—C bonded.

17. A process for the preparation of an amphiphilic silicone composition of claim 1, comprising reacting an Si—H containing organopolysiloxane containing groups of the formula $R_{3-c}H_cSi—O,(R^1{}_2SiO)_i,(R^1HSiO)_j(H_2SiO)_k,$ and Si $R_{3-c}H_c$ wherein c is 1 or 2, in a hydrosilylation reaction, wherein i, j, and k are such that following hydrosilylation an amphiphilic silicone product of the formula (I) is obtained;
with hydrosilylatable reactants comprising
(a) at least one arylalkene;
(b) at least one long chain alkene having 8 to 45 carbon atoms; and
(c) at least one oxygen-containing hydrophilic group having a molecular weight greater than 100 Daltons and bearing at least one hydrosilylatable hydrocarbon group,
the reaction of the Si—H containing organopolysiloxanes and hydrosilylatable compounds (a), (b), and (c) taking place together or in any order, neat or in the presence of an organic solvent, and in the presence of at least one hydrosilylation catalyst, to form an amphiphilic silicone of formula (I).

18. The process of claim 17, wherein (a), (b), and (c) are reacted in at least two steps, a first step including (a).

19. The process of claim 17, wherein each of (a), (b), and (c) are added stepwise.

20. The process of claim 19, wherein the order of the stepwise additions is (a), then (b), then (c).

21. The process of claim 17, wherein the Si—H-containing organopolysiloxane is an organopolysiloxane containing methylhydrogensiloxy units, phenylhydrogensiloxy units, or mixtures thereof, and optionally dihydrogensiloxy units.

22. The process of claim 21, wherein the Si—H-containing organopolysiloxane further contains dimethylsiloxy groups, diphenylsiloxy groups, phenylmethylsiloxy groups, or mixtures thereof, and has at least one —$SiR_3$ group selected from the group consisting of trimethylsilyl, dimethylhydrogensilyl, and hydroxydimethylsilyl.

23. The process of claim 17, wherein the at least one arylalkene (a) is selected from the group consisting of styrene, α-methylstyrene, and vinylnaphthalene.

24. The process of claim 17, wherein the at least one long chain alkene (b) contains from 8 to 26 carbon atoms.

25. The process of claim 17, wherein the reactant (c) comprises an alkenyl-group terminated polyoxyalkylene polyether selected from the group consisting of homopolyoxyethylene glycols, homopolyoxypropylene glycols, and copolymeric poly(oxyethylene/oxypropylene) polyethers, the polyoxyalkylene polyethers also bearing a terminal group selected from $C_{1-30}$ alkyl, hydroxyl, and groups other than $C_{1-30}$ alkyl and hydroxyl which do not interfere with hydrosilylation of the reactant (c).

26. The process of claim 17, further comprising also reacting at least one of a hydrocarbon having 4 to 30 carbon atoms and two sites of ethylenic unsaturation or a hydrophilic group bearing two sites of ethylenic unsaturation.

27. The process of claim 17, further comprising admixing the amphiphilic silicone with ingredients of a personal care product.

28. The process of claim 27, wherein the personal care product is selected from the group consisting of hair shampoos, hair conditioners, hair shine sprays, hair pomades, hair mousses, hair gels, hair creams, skin care lotions and creams, lip stick, lip gloss, and other cosmetics for the face or eye area where shine/gloss is desired.

* * * * *